United States Patent
Ryan

(10) Patent No.: US 6,265,148 B1
(45) Date of Patent: *Jul. 24, 2001

(54) BLOOD CONTROL AND SYSTEM FOR ERYTHROCYTE SEDIMENTATION MEASUREMENT

(75) Inventor: Wayne L. Ryan, Omaha, NE (US)

(73) Assignee: Streck Laboratories, Inc., La Vista, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/558,242

(22) Filed: Apr. 24, 2000

Related U.S. Application Data

(63) Continuation-in-part of application No. 09/324,279, filed on Jun. 2, 1999, now Pat. No. 6,124,089, which is a continuation-in-part of application No. 09/303,719, filed on Apr. 30, 1999, now abandoned.

(51) Int. Cl.⁷ ............... C12Q 1/00; C12Q 1/24; G01N 1/30
(52) U.S. Cl. ........ 435/4; 435/283.1; 435/40.5; 435/30
(58) Field of Search .......... 435/4, 283.1, 40.5, 435/30

(56) References Cited

U.S. PATENT DOCUMENTS

| | | | |
|---|---|---|---|
| 2,102,785 | 12/1937 | Brooks | 435/4 |
| 2,727,838 | 12/1955 | Dalter | 435/4 |
| 2,848,368 | 8/1958 | Witt | 435/4 |
| 2,926,764 | 3/1960 | Hultin et al. | 435/4 |
| 3,660,037 | 5/1972 | Sokol | 435/4 |
| 3,873,467 | 3/1975 | Hunt | 435/4 |
| 4,064,118 | 12/1977 | Wong | 435/4 |
| 4,102,810 | 7/1978 | Armstrong | 435/4 |
| 4,264,470 | 4/1981 | Chastain, Jr. et al. | 435/4 |
| 4,299,726 | 11/1981 | Crews et al. | 435/4 |

(List continued on next page.)

FOREIGN PATENT DOCUMENTS

| | | |
|---|---|---|
| 01199158 | 8/1989 | (JP) . |
| PCT/US96/15628 | 4/1997 | (WO) . |

OTHER PUBLICATIONS

Thomas, et al., Calibration and Validation for Erythrocyte Sedimentation Tests, Arch. Pathol. Lab. Med., vol. 117, Jul. 1993, p. 719–723.

Excerpt from Sedimatic™ User Manual & Technical Reference by Analysis Instrument.

Equinox–Sed Rate product information (1998).

ESR CHEX and ESR 8 Product Information (1999).

Bull et al., The Zeta Sedimentation Ratio, Blood, 40(4): 550 (Oct. 1972).

De Castro et al., Valoracion de un sistema alternativo totalmente automatizado para la determinacion de law velocidad de sedimentacio globular, Sangre 34(1):4–9 (1989).

International Committee for Standarization in haematology (ICSH), Recommendation for Measurement of Erythrocyte Sedimentation Rate of Human Blood, Am. J. Clin. Pathol. 68:505–512 (1981).

(List continued on next page.)

Primary Examiner—Louise N. Leary
(74) Attorney, Agent, or Firm—Dobrusin Darden Thennisch & Lorenz PC

(57) ABSTRACT

A control and system for blood testing, including a control having morphologically fixed and stabilized blood cells that have been added to a diluent. The control and system can be used advantageously for indirect acute protein plasma measurement, including erythrocyte sedimentation rate testing.

5 Claims, 6 Drawing Sheets

U.S. PATENT DOCUMENTS

| | | | |
|---|---|---|---|
| 4,324,686 | 4/1982 | Mundschenk | 435/4 |
| 4,358,394 | 11/1982 | Crew et al. | 435/4 |
| 4,436,821 | 3/1984 | Ryan | 435/4 |
| 4,489,162 | 12/1984 | Hawkins et al. | 435/4 |
| 4,572,899 | 2/1986 | Walker et al. | 435/4 |
| 4,704,364 | 11/1987 | Carver et al. | 435/4 |
| 4,777,139 | 10/1988 | Wong et al. | 435/4 |
| 5,316,729 | 5/1994 | Orth et al. | 435/4 |
| 5,328,822 | 7/1994 | McKinney | 435/4 |
| 5,380,664 | 1/1995 | Carver et al. | 435/4 |
| 5,482,829 | 1/1996 | Kass et al. | 435/4 |
| 5,529,933 | 6/1996 | Young et al. | 435/4 |
| 5,863,799 | 1/1999 | Hengstenberg | 435/4 |
| 5,888,822 | 3/1999 | Hengstenberg | 435/4 |
| 5,895,760 | 4/1999 | Chen et al. | 435/4 |
| 5,895,769 | 4/1999 | Chen et al. | 435/4 |
| 6,017,764 | 1/2000 | Chen et al. | 435/4 |
| 6,124,089 * | 9/2000 | Ryan | 435/4 |

OTHER PUBLICATIONS

International Committee for Standarization in Haematology (ICSH), Reference Method for the Erthrocyte Sedimentation Rate (ESR) Test on Human Blood, Br.J. Haematol. 24:671(1972).

Jou et al., Evalucion de un sistema totalmente automatico para realizar la velocidad de sedimentacion globular, Sangre 33:474–478 (1988).

Product Brochure, Dispette®, Ulster Scientific, Inc., New Paltz, NY date unknown.

Product Brochure, Dispette®2, User Scientific, Inc., New Paltz, NY, date unknown.

Todd–Sanford Clinical Diagnosis by Laboratory Method (15$^{th}$ edition), *Erythrocyte Sedentimation Rate* (ESR, edited by Davidsohn, I., and Henry, J., pp. 133–135, WB Sauders Company, London, Toronto (1974).

Landaas et al., "The Quality of Laboratory Analyses in the Primary Health Care," Scan J. Prim Health Care 1986; 4:169–73.

Harkness, J. A New Instrument for the Meaurement of Plasma Viscosity. Lancet. 1963; 280–281.

Fahraeus, Robin, Acta Medica Scandinavica. 1921; 55 (Excerpt).

Westergren, A., Studies of the Suspension Stability of the Blood in Pulmonary Tuberculosis. Acta Medica Scandinavica. 1921; 54: 247–282.

Kushner, I. The Phenomenon of the Acute Phase Response. Ann N.Y. Acad. Sci. 1982; 389: 39–48.

Gabay, Cem et al. Acute–Phase Proteins and Other Systemic Responses to Inflammation. The New England Journal of Medicine, 448–454.

Moshage, Han., Cytokines and the Hepatic Acute Phase Response. Journal of Pathology. 1997; 181: 257–266.

Cooke, B.M. et al., Automated Measurement of Plasma Viscosity by Capillary Viscomenter. J. Clin. Pathol. 1988; 41: 1213–1216.

Stuart, J., Kenny, M.W. Blood Rheology. J. Clin . Path. 1980; 33: 417–429.

Guidelines on Selection of Laboratory Tests for Monitoring the Acute Phase Response. J. Clin Pathol. 1988; 41; 1203–1212.

The Clinical Laboratory Improvement Act (CLIA–88), 42 C.F.R., Part 493, Subpart K (12).

Fujil, T. Shape Changes of Human Erythrocytes Induced by Various Amphiphathic Drugs Acting on the Membrane of the Intact Cells. Biochem J. Pharmacology. 1979; 28: 613–620.

Hema–Trol/Sedratrol Product Information.

Gregersen, M. et al., Relation of Molecular Size of Dextran to its Effects on the Rheological Properties of Blood (28198). Proceedings of Society for Experiemental Biology & Medicine. 883–886.

Strauss, R., In vitro Comparison of the Erythrocyte Sedimenting Properties of Dextran, Hydroxyethyl Starch and New Low–Molecular–Weight Hydroxyethyl Starch. Vox Sang 1979: 37;268–271.

Meiselman, H., The Influence of Dextran on the Sedimentation Behavior of Human Red Cells: Macro and Micro Studies. 5$^{th}$ Europ. Conf. Microcirculation, Gothenburg 1968. Bibl. Anat., No. 10; pp. 20–31.

* cited by examiner

BLOOD CONTROL AND SYSTEM FOR ERYTHROCYTE SEDIMENTATION MEASUREMENT

This application is a continuation-in-part of commonly owned copending U.S. patent application, Ser. No. 09/324,279 filed Jun. 2, 1999, which is a C.J.P. of 09/303,719 filed Apr. 30, 1999, abandoned and having the same title as this application, the contents of which are hereby expressly incorporated by reference herein.

BACKGROUND OF THE INVENTION

1. Technical Field of the Invention

The present invention relates to blood controls and more particularly to controls for use in indirect acute phase protein measurement tests.

2. Background

There are various methods that have been described which result in the indirect measurement of the acute-phase (inflammatory response) proteins, including the erythrocyte sedimentation rate (ESR) test, the Zeta Sedimentation Ratio Test, and Plasma Viscosity Test. See Bull, B., Brailsford, D. The Zeta Sedimentation Ratio. Blood. 1972; 40: 550–559. Harkness, J. A New Instrument for the Measurement of Plasma Viscosity. Lancet. 1963;280–281.

By way of the history, possibly the first detailed method for indirectly measuring (by erythrocyte sedimentation) acute-phase proteins was described by Fahraeus in 1921. Fahraeus, Robin. Acta Medica Scandinavica. 1921; 55:1–228. The test was later modified by Fahraeus and Westergren. Westergren, A. Studies of the Suspension Stability of the Blood in Pulmonary Tuberculosis. Acta Medica Scandinavica. 1921; 54:247–282. Although there have been many modifications of this manual test, the basic method has survived. The method involves diluting blood, filling a standardized tube, and measuring the distance the red cells settle in a specific time interval.

The erythrocyte sedimentation rate test (ESR) measures the proteins of blood that are increased by inflammation. The presence of these proteins causes an increase in viscosity and also causes the red cells to sediment more rapidly. The mechanisms for the changes in these proteins are better understood today than when the test was introduced by Fahraeus in 1921. Fahraeus, Robin. Acta Medica Scandinavica. 1921; 55: 1–228 (page 121). However, he recognized the importance of fibrinogen and globulins which are the major proteins producing an increased ESR.

It is believed that the basis for the increased sedimentation is due to a group of proteins called acute phase proteins. These are macromolecules of the plasma such as fibrinogen and the globulins. The proteins are synthesized in the liver and their levels in the plasma rise with inflammation. Kushner, I. The Phenomenon of the Acute Phase Response. Ann N.Y. Acad. Sci. 1982; 389: 39–48. Han Moshage divides the acute phase proteins into two groups: (1) Type I proteins, which include serum amyloid, C-reactive protein, Complement C3, haptoglobin and α1-acid glycoprotein. These are induced by interleukin-1-like cytokines such as IL-1α, IL-1B, TNF-α, and TNF-B; and (2) Type II proteins, which are induced by IL-6 like cytokines which include IL-61, LIF, IL-II, OSM, CNTF, and CT-1. The IL-6 will synergize with IL-1 to induce the Type I proteins of the cytokines. IL-6 is believed to be the main cause of the induction of acute-phase proteins. Gabay, Cem et al. Acute-Phase Proteins and Other Systemic Responses to Inflammation. The New England Journal of Medicine. 448–454. Moshage, Han. Cytokines and the Hepatic Acute Phase Response. Journal of Pathology. 1997; 181:257–266.

Coulter Corporation has offered an instrument, the ZETAFUGE, for determining the zeta sedimentation ratio. Bull and Brailsford (Bull, B., Brailsford, D. The Zeta Sedimentation Ratio. Blood 1972; 40; 550–559) have described a method for making controls or "standards" for this system.

The plasma viscosity test is commonly employed for indirectly measuring acute phase proteins in the United Kingdom. One suitable instrument, the Viscometer, and controls for it are manufactured by Coulter Corporation. This technique was described by Cooke and Stuart in 1988. An earlier article describing this methodology was published in the J. Clinical Pathology in 1980 by Stuart and Kenny. Cooke, B. M. et al. Automated Measurement of Plasma Viscosity by Capillary Viscomenter. J. Clin Pathol. 1988; 41:1213–1216. Stuart, J., Kenny, M. W. Blood Rheology. J. Clin Path. 1980; 33:417–429.

Other automated instruments have appeared on the market. Examples include the Ves-Matic®, Mini-Ves®, Sed-Mat®, and ESR-8/Sedimatic 8™.

Methods for determining acute phase proteins can be influenced by numerous factors. Several of these relate to the type of tube used and other environmental conditions. For instance, bench-top vibration, temperature and tube angle may affect rates obtained. The need for using control preparations for these methods is well established. The ICSH Committee has addressed this issue in 1988 (International Committee for Standardization in Haematoloy (Expert panel on Blood Rheology). Guidelines on Selection of Laboratory Tests for Monitoring the Acute Phase Response. J. Clin Pathol. 1988; 41; 1203–1212) and 1993 (Thomas, Robert et al. Calibration and Validation for Erythrocyte Sedimentation Tests. Arch Pathol Lab Med. 1993; 1 17; 719–723). They describe the use of selected blood specimens for quality controlling the "routine" ESR method by comparison to the "reference" method. One control for use in a particular ESR test is that addressed in U.S. Pat. Nos. 5,863,799 and 5,888,822. The Clinical Laboratory Improvement Act (CLIA-88) mandated that control preparations be used for all automated instruments. See. e.g., 42 C.F.R., Part 493, Subpart K (12), incorporated by reference herein. Prior to CLIA-88, the use of controls was not mandated.

From the above it is clear that the concept of using control preparations for monitoring all three methods has been well known. Unmodified human blood can provide controls which have limited stability. In those instances, the controls are used in applications where the stability that is desired is less than several months.

SUMMARY OF THE INVENTION

One preferred method for achieving long-term stability in a control includes the combination of using a citrate-based diluent, and heating the cells above room temperature and preferably below about 51° C. The cells are fixed morphologically, such as with a suitable aldehyde (e.g., glutaraldehyde). An aggregating agent also is preferably employed in solution to facilitate an appropriate predetermined sedimentation rate. Controls made according to the present invention are useful for acute phase protein measurement in systems using a manual, semiautomated or automated test apparatus. The controls are stable over long-term and short-term intervals.

Preparation of a long-term stable (i.e., capable of achieving up to several months of stability or shelf-life) control desirably avoids reliance on the use of unmodified fibrinogen and normal RBC. Accordingly, the present control and system of the present invention provides an improved approach to indirect acute phase protein measurement. They afford the ability to have stable controls with relatively long shelf-lives, and with relative ease of manufacture.

DETAILED DESCRIPTION OF THE PREFERRED EMBODIMENT

Figure 1:
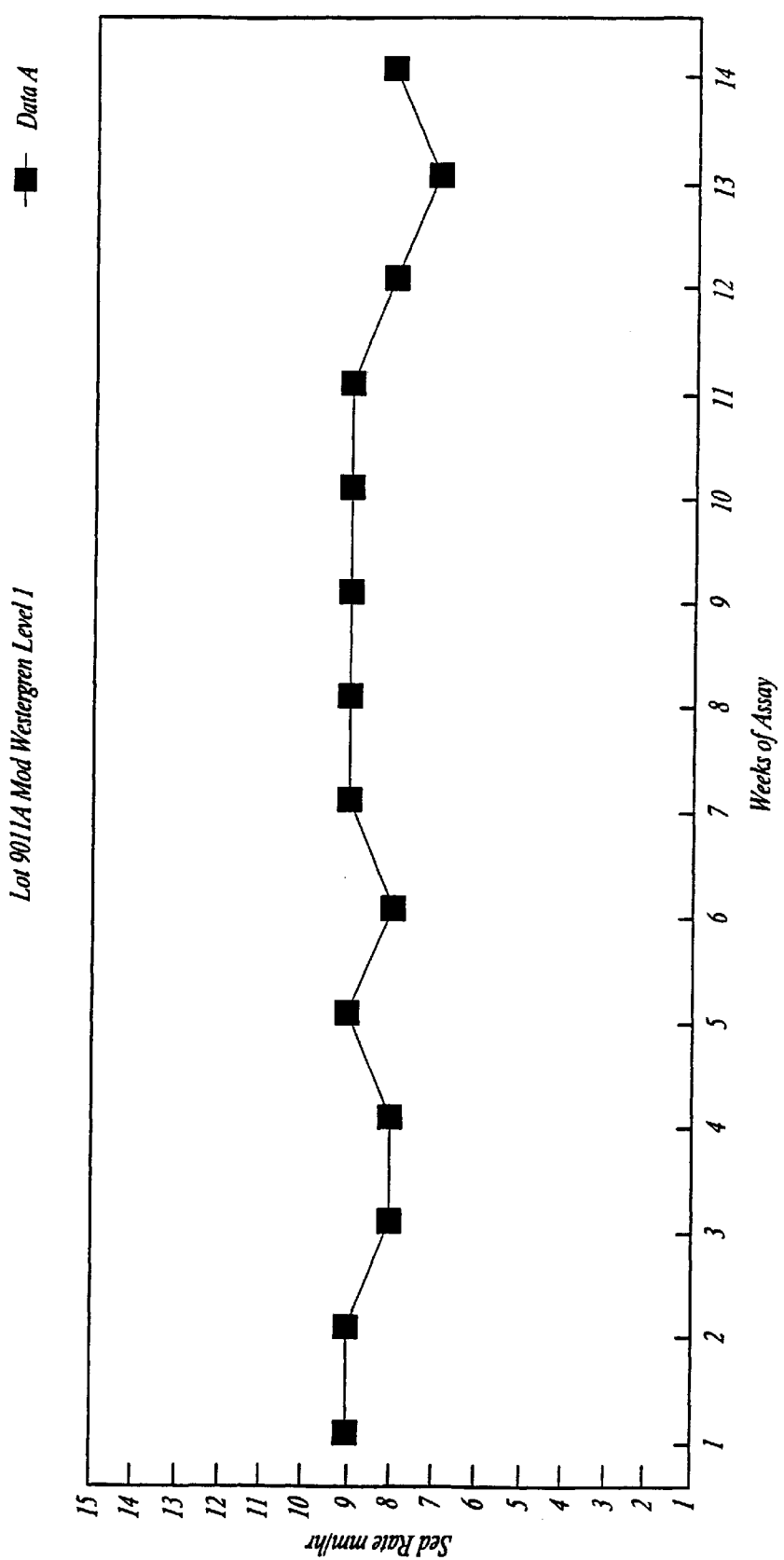
FIGS. 1–6 are some of the many examples of test results obtainable by use of the control and system of the present invention.

To prepare a preferred control of the present invention, a predetermined amount of a cell source (e.g., blood) is provided. The cell source is washed to remove undesired constituents, and provides a source of washed cells. The washed cells are fixed morphologically. The cells are stabilized and combined with an aggregating agent.

More specifically, when a blood source for providing red blood cells (RBC) is used, the starting blood is washed substantially free of plasma, platelets, and leukocytes preferably with a saline solution, such as one containing 1.5% polyethylene glycol-(20)(PEG-20K). This causes the red cells to aggregate and settle. After settling, the supernatant is removed. This is repeated multiple times (e.g., three times) to obtain washed red cells substantially free of contaminants. The starting blood may be from any suitable source and may be, for example, human or porcine blood. In an alternative embodiment, other surrogate RBC can be used, being prepared from any known method.

The washed cells are suspended in a diluent (e.g., a citrate diluent as disclosed herein in Table I) to a suitable concentration, e.g., in a range of about $3.9 \times 10^6$ to about $4.1 \times 10^6$ cells/mm$^3$, and more preferably about $4.0 \times 10^6$ cells/mm$^3$. A fixing agent (e.g., a suitable aldehyde, such as glutaraldehyde) is added. Preferably, when using glutaraldehyde it is added so that a final concentration (after final dilution) of about 0.08 g/l to about 0.48 g/l, and more preferably about 0.24 g/l glutaraldehyde, is attained. After a suitable period of time (e.g., about 24 hours), the cells are again washed with the diluent and suspended at a concentration of about $3.9 \times 10^6$ to about $4.1 \times 10^6$ cells/mm$^3$, and more preferably about $4.0 \times 10^6$ cells/mm$^3$.

Preferably, the diluent includes about 0.3% to about 1.1% by weight of a sodium citrate solution and may be comprised of one or more constituents which enhance or maintain cell surface structure, characteristics, morphology, or stability, or act as chelating agents, buffers, osmotic stabilizers, biological salts, or anti-microbial agents.

TABLE I

| Citrate Solution | Saline Solution |
| --- | --- |
| 5.0 g/l Polyethylene Glycol 20,000 | 8.0 g/l NaCl |
| 2.0 g/l Ethylenediaminetetra-acetic acid, Disodium Salt | 15.0 g/l Polyethylene Glycol 20,000 Plus antimicrobials |
| 7.5 g/l Magnesium Gluconate | |
| 7.0 g/l Sodium Citrate, trisodium dihydrate | |
| Plus antimicrobials | |

The cells are heated, such as by placing them in bottles in a water bath at elevated temperature, (e.g., several degrees greater than room temperature, preferably greater than about 15° C. higher than room temperature, more preferably in the range of about 48 to about 51° C., and more preferably about 49 to about 50° C.). Heating is continued for a sufficient time to achieve desired stability. The heating preferably is maintained to result in the formation of stabilized cells of a predetermined shape (e.g., discs) in at least about 90% of the cells, more preferably at least about 95% of the cells, and still more preferably about 99% of the cells.

Further, the heating preferably is done for sufficient time and at sufficient temperature to denature at least a portion of the cell surface proteins. For instance, the heating step is preferably done at about 48° to about 51° C. (and more preferably about 49° to about 50° C.) for a period of 60 to about 75 minutes or more. Less heat may be used (e.g., as little as about 2° C. cooler), but it will produce a product with shorter shelf life. Moreover, at temperatures over about 51° C. the red cells may become permanently altered (thus affecting stability), as evidenced by the development of many small vesicles in the solution. Thus, temperature conditions advantageously can be varied to selectively adjust desired product shelf-life.

The bottles are combined into two pools. To each pool is added a suitable agent for aggregating the cells, preferably a macromolecule having suitable charge characteristics (e.g., methylcellulose). A preferred methylcellulose has a viscosity of about 25 cps and is added between about 0.1 wght/vol % for a low aggregation level and about 0.5% methylcellulose for the high aggregation level.

The agent for aggregating the cells is dissolved in solution in the diluent, so that the resulting product only contains two components, the diluent and the blood cells. To illustrate, a stock solution of aggregating agent is prepared. In one embodiment, for instance, 2% stock of methyl cellulose (25 cps) is made by heating about 800 ml of distilled water to just below the water's boiling point, and more preferably to a temperature of about 90–96° C.

About 20 mg of methylcellulose is added slowly to the heated water with constant stirring. The resulting slurry mixture of wetted aggregating agent is continuously mixed for a suitable period, e.g., about one hour. About 200 ml cold water (e.g., near freezing, and preferably about 1–6° C.) is added to the slurry and mixed by stirring for about 30 minutes.

The stock solution is cooled (e.g., to about 0° C.) and continuously mixed until the solubility temperature of the aggregation agent solution is reached (in this illustration about 0 to 4° C.). Upon achieving a homogenous solution, the stock solution can be stored at a suitable temperature (e.g., about 6° C. to room temperature for a methyl cellulose solution).

Illustrative examples of diluent prepared with dissolved methylcellulose are shown below for two different levels. The solutions are admixed and filtered before preparing the final product.

1. 50% 2x (double concentration) citrate solution (Table I)+2% BSA
   (Bovine Serum Albumin)
   6% 2% methyl cellulose stock
   44% distilled water
2. 50% citrate solution (Table I)+20% BSA
   20% 2% methylcellulose stock
   30% distilled water While other agents might be used to cause erythrocyte aggregation and sedimentation (Table II), as can be seen, not all agents perform similarly.

TABLE II

OTHER AGENTS WITH CITRATE DILUENT ESR METHOD

| Agent | (ESR Method mm/hr) | | |
|---|---|---|---|
| | Wintrobe | Mod. Westergren | Mini Ves |
| 0.5% PVP* (360,000) | 28 | 32 | 62 |
| 1% PVP | 36 | 51 | 90 |
| 2% PVP | 64 | 96 | >140 |
| 1% Dextran (242,000) | 14 | 17 | 38 |
| 2% Dextran | 23 | 31 | 67 |
| 4% Dextran | 36 | 60 | 114 |
| 0.5% PVP (360,000) | 10 | 15 | 39 |
| 1% PVP | 15 | 17 | 38 |
| 2% PVP | 15 | 28 | 67 |
| 1% Dextran (242,000) | 4 | 4 | 16 |
| 2% Dextran | 8 | 7 | 27 |
| 4% Dextran | 12 | 15 | 50 |

*PVP - polyvinylpyrolidine
Cells were fixed in 0.24 g/l glut in Citrate and heated in citrate at 50° C. for 75 minutes.
Aggregating agents were in citrate diluent.

The stability of this product is shown in the accompanying figures. In particular, results on one manual and two automatic instruments for three to four months are shown in FIGS. 1–6 (discussed herein in the Examples).

An alternative method to obtain generally uniform cell shape is also used when the RBC do not initially have a disc shape. If they are significantly crenated, they may be first treated (e.g., by treating the cells with a suitable drug) to induce shape changes in the RBC. membrane. After addition of the drug, the cells are fixed (e.g., with glutaraldehyde at about 0.24 g/l and then heated to about 48°–50° C. Examples of drugs which may be used are amphipathic drugs, such as phenothiazine drugs, and particularly chlorpromazine, promethazine or a combination. See Fujil, T. Shape Changes of Human Erythrocytes Induced by Various Amphipathic Drugs Acting on the Membrane of the Intact Cells. Biochem J. Pharmacology. 1979,28:613–620. When added to red cells at concentrations of 0.001%–0.01% w/v, the shape change ordinarily occurs within a few minutes. Then the cells may be processed according to known techniques to obtain substantially uniform shapes.

It should be appreciated that other additives may be incorporated into the final control to obtain desired characteristics. Examples include those addressed in Example 5. Likewise, as seen from the Example and elsewhere herein, various additives may be used to help prepare the blood cells, prior to incorporation into the diluent.

The systems of the present invention contemplate the use of a control of the present invention with erythrocyte sedimentation measurement instruments, including manual, semiautomated and automated instruments. Examples include the classical Westergren, Modified Westergren, Wintrobe, ESR-8 (available through Streck Laboratories (Omaha, Nebr.)), Ves-Matic®, and Mini-Ves ®. When used, the system of the present invention satisfies CLIA-88 requirements.

Controls may be provided at different sedimentation levels (e.g., less than 20 mm/hr and greater than 30 mm/hr or as otherwise desired). Controls may be supplied as part of a kit for use with the instruments. For instance, a plurality of suitable vials or reservoirs having a predetermining volume (e.g., about 9 ml), preferably having pierceable cap, may be provided. Any suitable rack having leveling indicators and adjustability may be used to hold the vials. The control of the present invention advantageously can exhibit 95-day closed vial, 31-day open-vial stability or both.

In more fully automated systems, the system includes a suitable computer for receiving, storing, or transmitting data about specimen(s) tested. Bar code reader devices can be used to identify specimens and transmit information. Printers and other peripheral devices can be incorporated into the system to help manage data.

The following examples are by way of illustration only and are not intended as limiting. As the skilled artisan will appreciate various modifications can be made within the scope of the present invention.

EXAMPLES

For each of the Examples 1–3, one lot is run designated herein as Lot 9011A.

Example 1

Manual-Modified Westergren Test

Modified Westergren tests are done using Ulster Medical Products Dispette®-2 tubes. These tubes come with a prefilled reservoir (containing sodium chloride) and a pierceable cap. The above discussed preferred control (having a citrate diluent) is added to the reservoir to the fill line, the cap is replaced and the solution is mixed by inversion 8–10 times. The marked pipette tube is then pushed through the pierceable cap and the resulting system is placed in a rack that has been leveled. Tests are run for 60 minutes before reading the results.

Tests are run in a room whose temperature is between 19°–22° C. Controls are allowed to equilibrate to room temperature for 20 minutes before being mixed thoroughly and test sample withdrawn.

Example 2

Automated-ESR-8 Test

ESR 8 tests are done by adding the control of Example 1 to the fill line of the prefilled (sodium citrate) vacuum tube for this automated system and the stopper top replaced. The tubes are then inverted end-to-end ten to twelve times and placed in the ESR 8 instrument for the test run. Tests are done using the Quick mode setting (30 minute run time).

Tests are run in a room whose temperature is between 19°–220° C. Controls are allowed to equilibrate to room temperature for 20 minutes before being mixed thoroughly and test samples withdrawn. This test system takes 2 ml of sample for each tube.

Example 3

Automated Mini Ves Test

Mini Ves tests are done by adding the control of Example 1 to the fill line of the prefilled (sodium citrate) vacuum tube for this automated system and the stopper top is replaced. The tubes are then inverted end-to-end ten to twelve times and placed in the Mini Ves instrument for the test run. This test is done in 20 minutes.

Tests are run in a room whose temperature is between 190°–22° C. Controls were allowed to equilibrate to room temperature for 20 minutes before being mixed thoroughly and test samples withdrawn. This test system takes 1 ml of sample for each tube.

Figure 2:
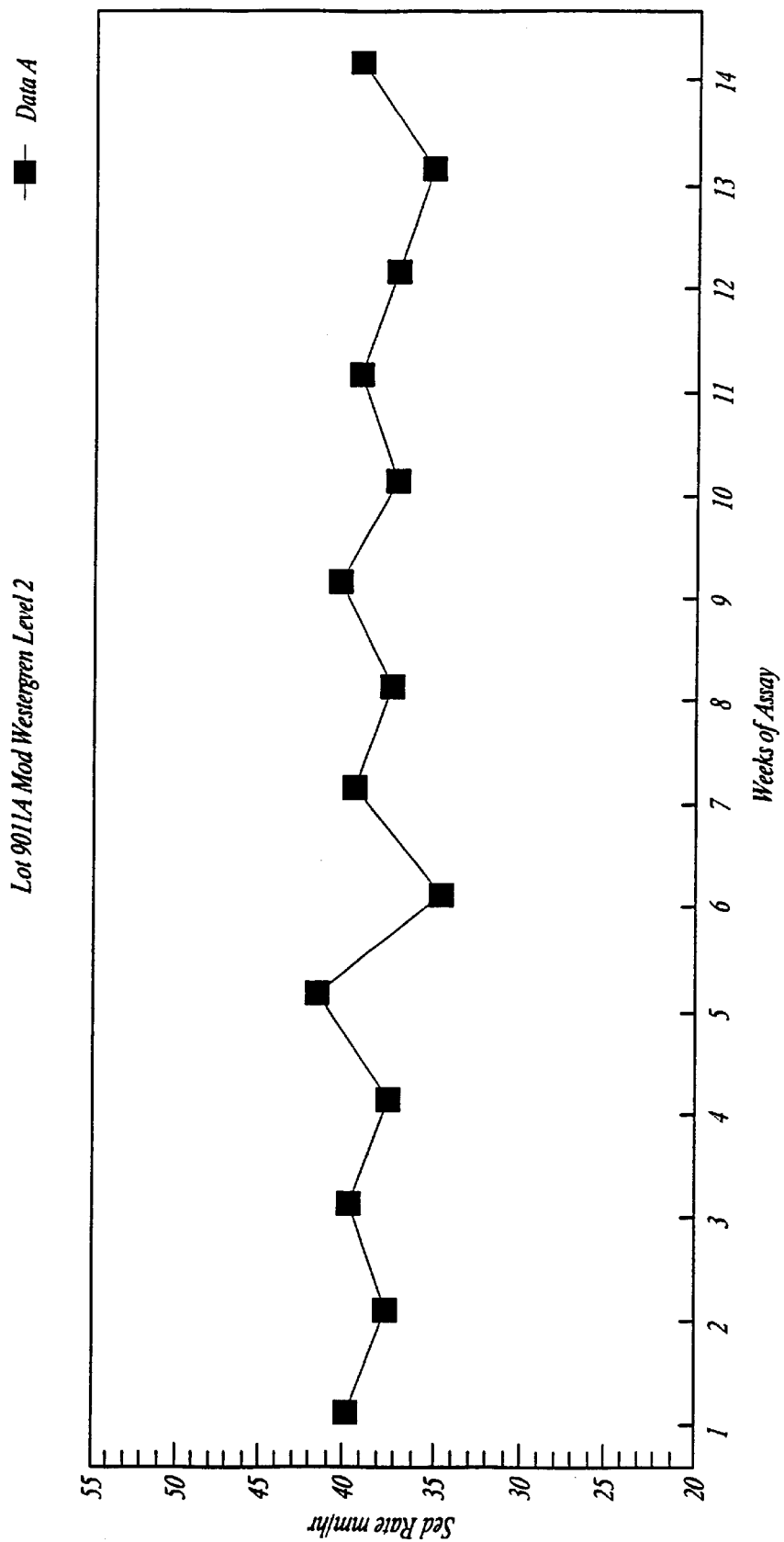
Figure 3:
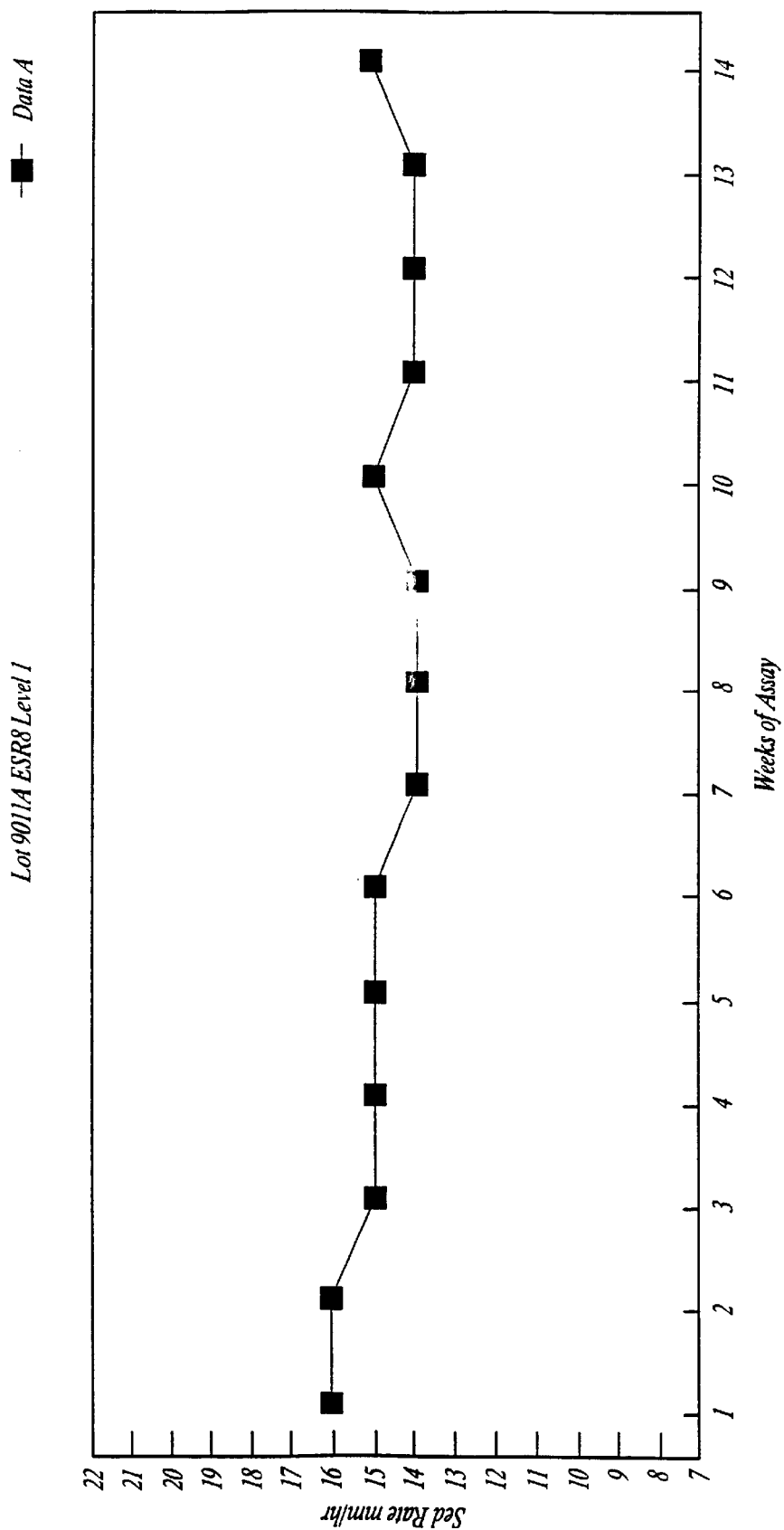
Figure 4:
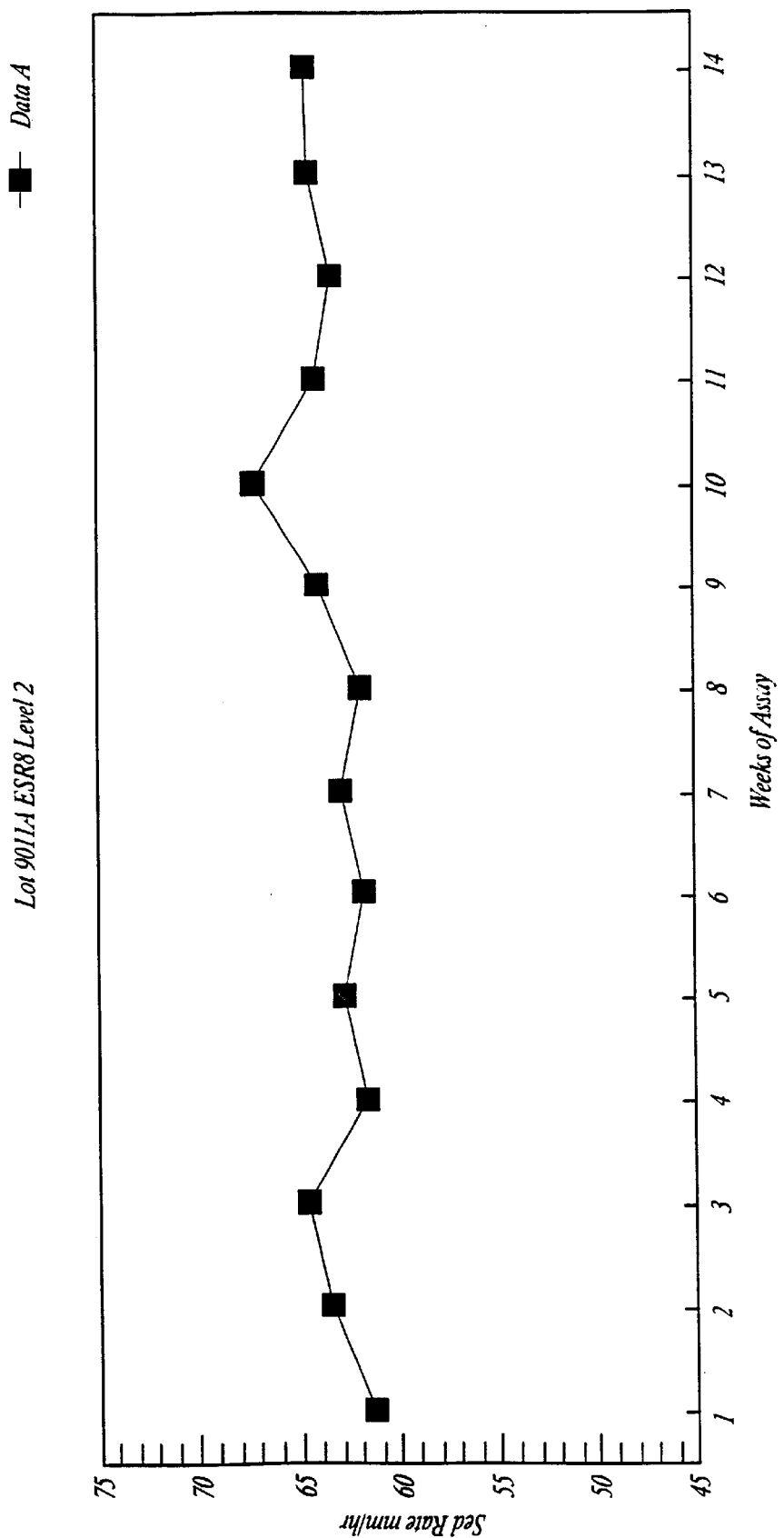
Figure 5:
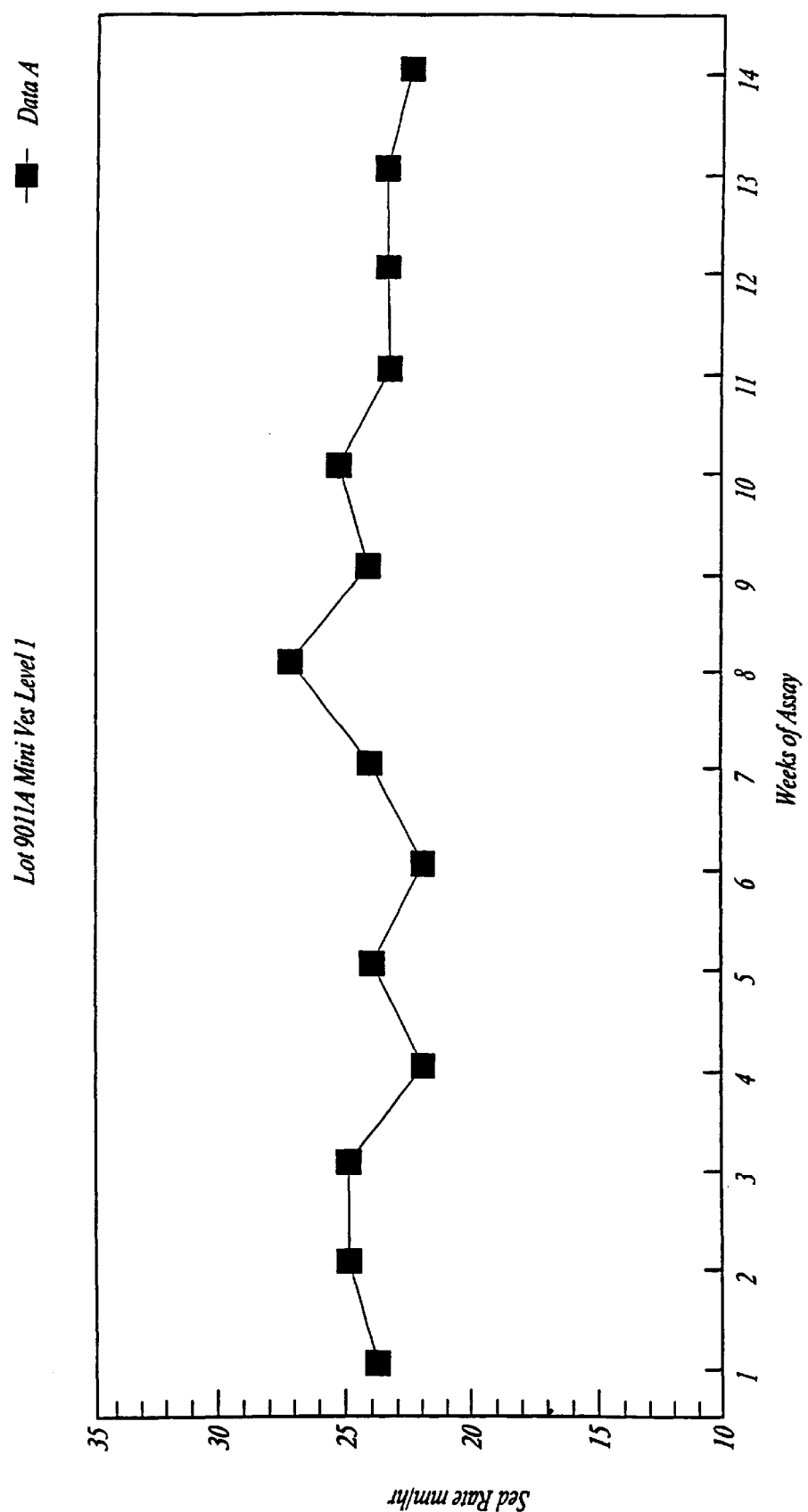
Figure 6:
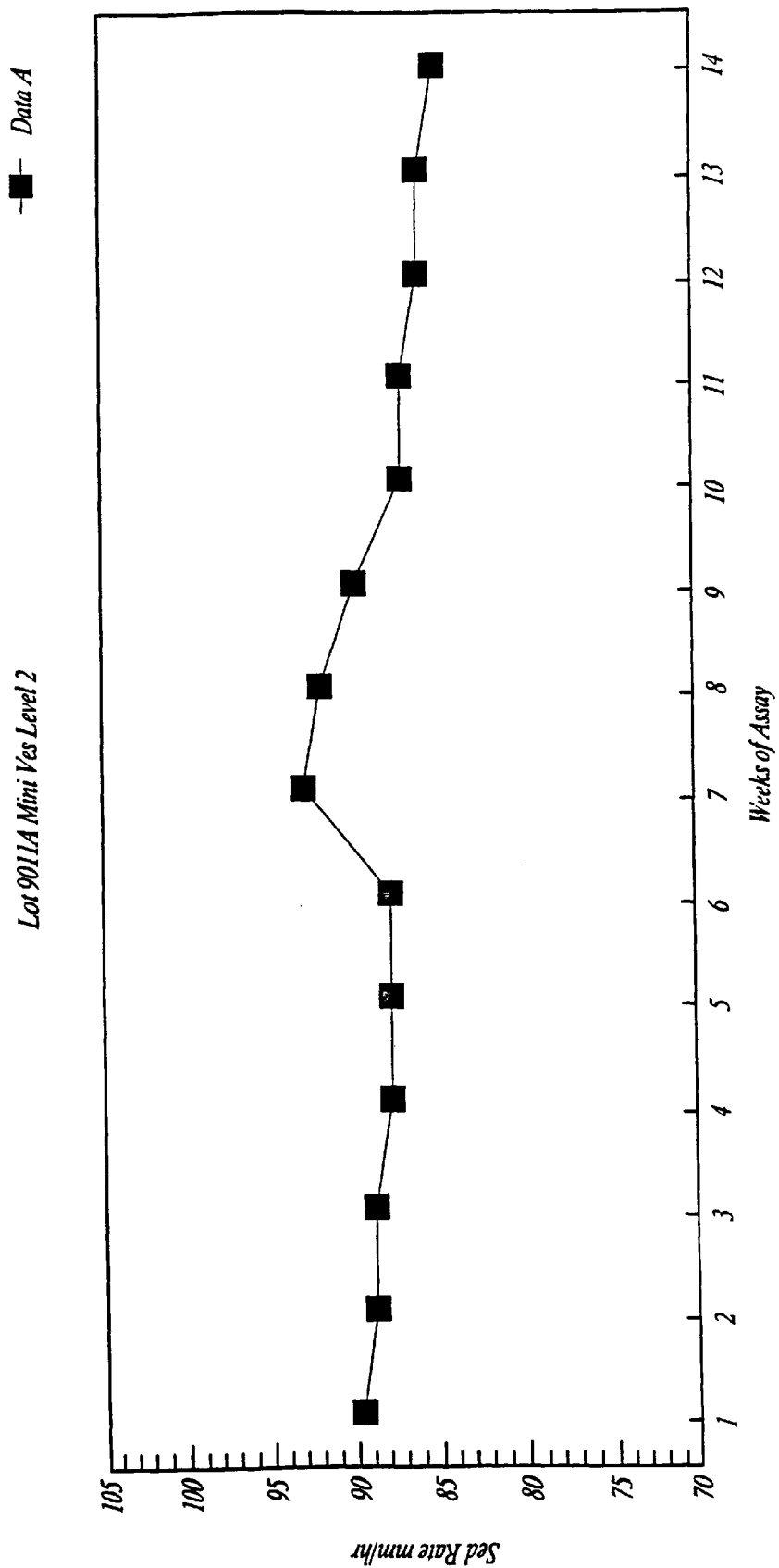

The results from the use of the controls run in Examples 1–3 in the different test systems are shown in the attached figures. FIGS. 1 and 2 show the results of Lot 9011A of Example 1. FIGS. 3 and 4 show the results of Lot 9011A of Example 2. FIGS. 5 and 6 show the results of Lot 9011A of Example 3. For each control, high and low levels are gleaned from the results.

The sedimentation of the red cells by methylcellulose is markedly decreased by heating. When the cells are heated at about 49°–50° C., the sedimentation rate is lowered, but the rate is stable. If cells are not heated or heated at a lesser temperature, the sedimentation is initially higher but within ten to fourteen days, the rate may drop. Data describing this finding is in the following Table III.

An additional finding is that phenothiazine drugs which affect the shape of the RBC can influence the sedimentation stability of the product. This effect is most pronounced when the cells are somewhat crenated.

Example 4

Samples are prepared and tested in accordance with the above disclosed subject matter. However, the heating step for stabilizing cells is varied to illustrate the relative effects of temperature. The results are in Table III.

All cells are placed in citrate diluent and fixed at 0.24 g/l glut before heating. Heating is done for 75 minutes at the above designated temperatures. After heating, cells are washed into methyl cellulose-citrate solution with various concentrations of methyl cellulose to give similar sedimentation rate recovery values.

TABLE III

EFFECT OF HEATING ON SEDIMENTATION STABILITY

| Heating Temp. | Instrument | (Units mm/hr.) Initial | 5 days | 21 days |
|---|---|---|---|---|
| No Heat | Mini Ves | 111 | 111 | 10 |
| 47° C. | | 97 | 97 | 62 |
| 50° C. | | 85 | 85 | 90 |
| No Heat | Mod. Westergren | 80 | 75 | 53 |
| 47° C. | | 62 | 79 | 34 |
| 50° C. | | 38 | 44 | 43 |
| No Heat | Wintrobe | 68 | 68 | 46 |
| 47° C. | | 58 | 62 | 32 |
| 50° C. | | 40 | 38 | 42 |

Example 5

An RBC control is prepared as follows and when used as a control, yields substantially identical results as the controls of Examples 1–3. Incoming RBCs are diluted in a saline solution of approximately the following composition:

Saline Solution
 8.0 g/l NaCl
 5.0 g/l Polyethylene Glycol 20,000
 Plus antimicrobials
and gravity settled overnight. The cells are then washed about two times in a saline solution.

The cells are filtered and washed in a citrate solution of approximately the following composition (preferably with about 0.01% phenergan):

Citrate Solution
 5.0 g/l Polyethylene Glycol 20,000
 2.0 g/l Ethylenediaminetetra-acetic acid, Disodium Salt
 7.5 g/l Magnesium Gluconate
 7.0 g/l Sodium Citrate, trisodium dihydrate
 Plus antimicrobials and then incubated overnight at approximately room temperature. The cells are then adjusted to a concentration of approximately $4.0–10^6/mm^3$, with about 250 ml per treatment bottle, and heated at about 50 C. for approximately 75 minutes. The cells are then fixed with glutaraldehyde in a citrate solution and washed into a citrate solution. The cells are then washed into a final ESR Chex diluent of approximately the following composition at about the indicated cell concentration:

Approximate Final Composition
 Methyl cellulose—25 cps (1.2 g/l level 1, 3.0 –5.0% g/l level 2)
 0.10 g/l Phenergan
 Treated and fixed cells at concentration of $2.2–2.5\times10^6/mm^3$
 Citrate solution of approximately:
  5.0 g/l Polyethylene Glycol 20,000
  2.0 g/l Ethylenediaminetetra-acetic acid, Disodium Salt
  7.5 g/l Magnesium Gluconate
  7.0 g/l Sodium Citrate, trisodium dihydrate
  Plus antimicrobials Although the invention has been described with particular reference to certain preferred embodiments thereof, variations and modifications can be effected within the spirit and scope of the following claims.

What is claimed is:

1. A control for use in an acute phase protein measurement test, comprising:
 a) a plurality of substantially uniformly shaped fixed cells;
 b) methylcellulose; and
 c) a citrate diluent.

2. The control of claim 1, wherein said cells are comprised of red blood cell surrogates.

3. The control of claim 1, wherein said cells are comprised of red blood cells.

4. The control of claim 1, wherein said cells are comprised of human cells.

5. The control of claim 1, wherein said cells are comprised of porcine cells.

* * * * *